United States Patent [19]

Tichy

[11] Patent Number: 5,086,789
[45] Date of Patent: Feb. 11, 1992

[54] WIND DEFLECTOR FOR THE EAR

[76] Inventor: James B. Tichy, P.O. Box 1308, Sausalito, Calif. 94966

[21] Appl. No.: 531,965

[22] Filed: Jun. 1, 1990

Related U.S. Application Data

[63] Continuation-in-part of Ser. No. 406,685, Sep. 13, 1989, abandoned.

[51] Int. Cl.$^5$ .............................................. A41D 21/00
[52] U.S. Cl. ...................................... 128/866; 2/209; 128/864
[58] Field of Search .................................. 2/209, 174; 128/864–867

[56] References Cited

U.S. PATENT DOCUMENTS

| | | |
|---|---|---|
| 437,602 | 8/1890 | Kaiser . |
| 1,768,068 | 6/1930 | Jauss . |
| 1,853,131 | 4/1932 | Lewis . |
| 2,537,201 | 1/1951 | Amfitheatrof ............... 181/25 |
| 2,672,864 | 3/1954 | Makara ....................... 128/152 |
| 3,728,741 | 4/1973 | Lepor ........................... 2/209 |
| 4,344,425 | 8/1982 | Strauss ....................... 128/864 |
| 4,616,643 | 10/1986 | Jung ........................... 128/866 |
| 4,660,229 | 4/1987 | Harris ......................... 128/866 |
| 4,670,911 | 6/1987 | Dunford ....................... 2/209 |
| 4,682,374 | 7/1987 | Geiser ......................... 2/209 |
| 4,713,843 | 12/1987 | Duncan ....................... 128/866 |
| 4,731,684 | 12/1988 | Schwartz ...................... 2/209 |

OTHER PUBLICATIONS

U. R. Kristiansen, O.K. ø Pettersen, 1978 Journal of Sound and Vibration, "Experiments on the Noise Heard by Human Beings When Exposed to Atmospheric Winds", 58(2), 285–291.

*Primary Examiner*—Robert A. Hafer
*Assistant Examiner*—Kerry Owens
*Attorney, Agent, or Firm*—Townsend and Townsend

[57] ABSTRACT

A wind deflector deflects wind away from the ear to reduce wind noise while ambient sound passes through to the inner ear so that the user's hearing is not substantially impaired.

26 Claims, 2 Drawing Sheets

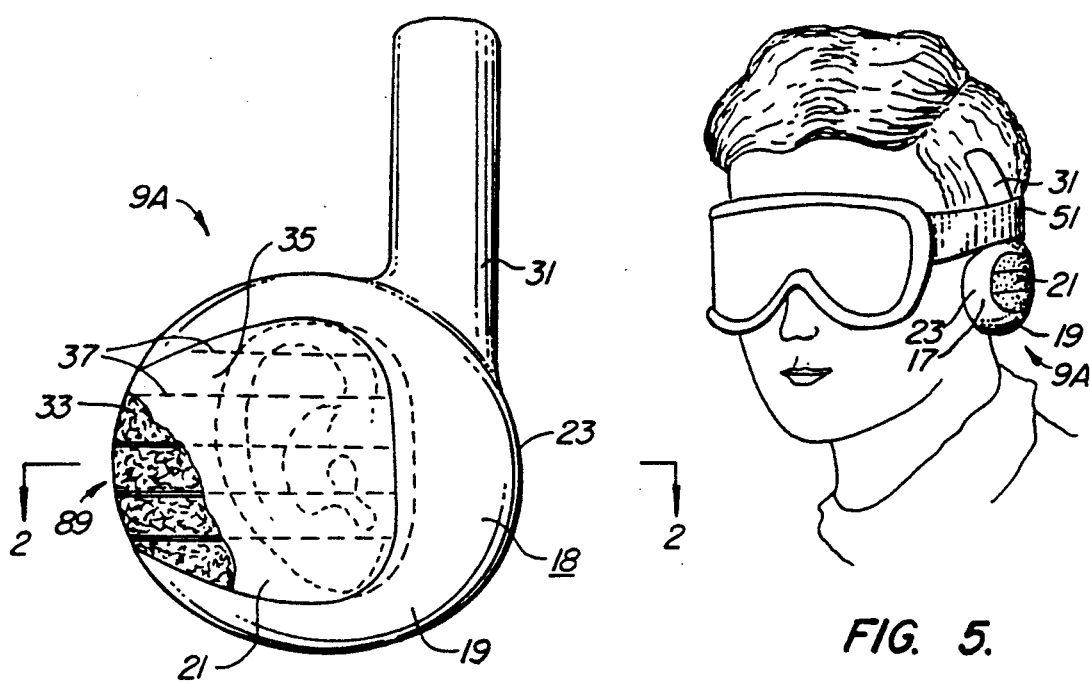
FIG. 1.
FIG. 5.
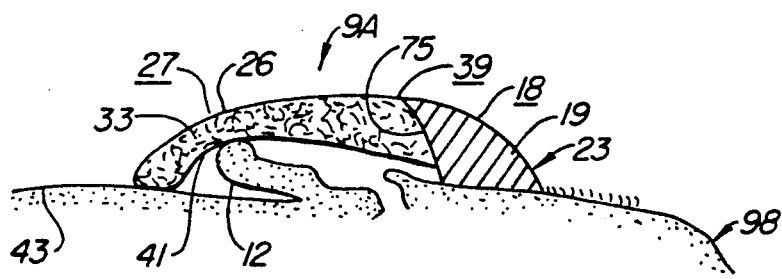
FIG. 2.
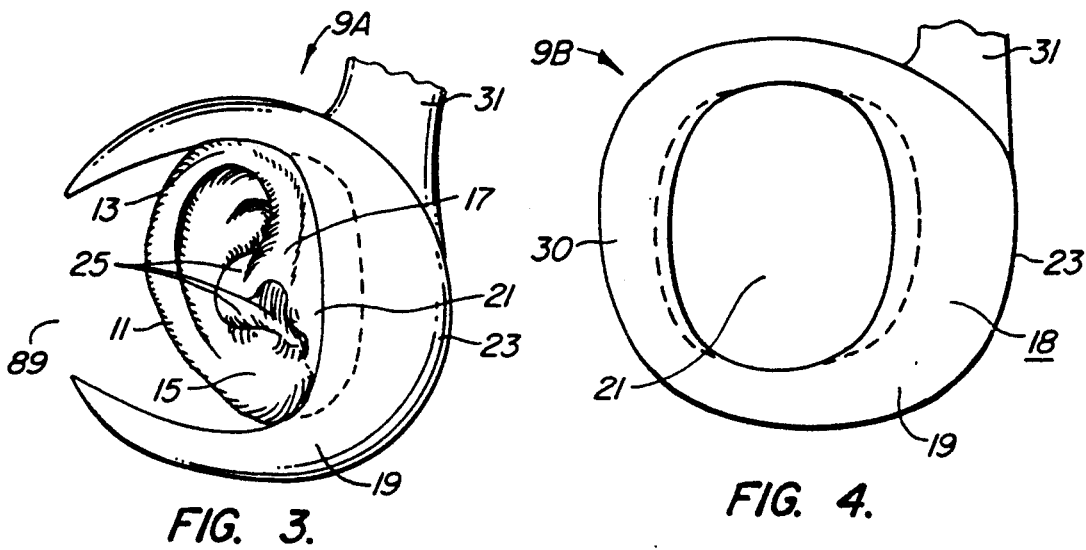
FIG. 3.
FIG. 4.

WIND DEFLECTOR FOR THE EAR

This application is a continuation-in-part of U.S. patent application Ser. No. 07/406,485 filed Sept. 13, 1989 now abandoned.

BACKGROUND OF THE INVENTION

The present invention relates generally to wind deflector apparel. More particularly, it concerns a device for smoothly redirecting wind away from the ear for the purpose of decreasing any personally heard wind noise generated by air flow past the ear and head, while at the same time permitting ambient sound to pass through unattenuated.

There are two main sources of perceived wind noise. In a head wind the first source is due to the shape of the head causing turbulence just behind the cheek bone, and is mainly responsible for the very low frequency noise. The second source appears to be due to stream flow by the concha which is the shallow cavity inside the ear just adjacent to the sensitive ear canal, and is apparently responsible for the higher frequency noise.

At low wind speeds, the combined noise spectrum creates a personal rumbling in the ear canal which gets louder and also higher in frequency as the wind speed increases. Unweighted measurements have been made of the noise created in the concha by the use of a microphone probe apparatus. See, U. R. Kristiansen, O.K.φ. Pettersen 1978 *Journal of Sound and Vibration*, "Experiments On The Noise Heard By Human Beings When Exposed To Atmospheric Winds", 58(2)285-291. For an average person facing a 21 mile per hour (mph) wind the noise spectrum was found to extend below 25 cycles per second (Hz) to about 150 Hz at an intensity of 92 decibels (db) above quiet hearing threshold. The noise spectrum then tapers off in intensity to 60 db at 2400 Hz. Articulation tests have shown that the band of speech frequencies most important for intelligibility is that extending from about 500 to 2500 Hz. The signal to noise ratio of speech to wind induced ear canal noise can significantly deteriorate for winds above 20 mph. This comes as no surprise to hard of hearing sufferers who have lost their high frequency sensitivity and must completely rely on the lower part of the hearing spectrum. Even bike riders, sailors, skiers, etc. with good hearing may have considerable difficulty hearing ambient sounds such as traffic, conversation between companions, safety warnings and certain sounds of nature. High relative wind speeds are not uncommon, e.g., by bicycling 15 mph into a 15 mph atmospheric wind the relative headwind is 30 mph. Then too, for those who simply stand still on a windy day, such as pedestrians, construction workers and field workers, the same noise can be heard with additional low frequency pulses.

There is the additional problem of fatigue. The apparent intensity of the wind seems to be greater when it can also be heard. Constant and especially gusty wind noise over a long period of time can create considerable fatigue, which if not corrected can reduce the enjoyment of an activity and can even turn to irritation. Worse, fatigue can also be a contributing factor in creating misjudgments and accidents. Some children are quite susceptible to wind induced noise in the ear.

For the most part, this is a problem people have learned to live with. Mechanical devices such as ear plugs and ear muffs are designed to protect the ear against very loud machinery noises. By their very nature they are not completely sound permeable but contain a considerable amount of sound resistant material.

Heavy duty earmuffs, that are primarily designed to warm the ears, generally handle wind noise abatement as a secondary feature. For instance, Geiser, U.S. Pat. No. 4,582,374, provides for open ventilator holes drilled or cast through an otherwise solid, heat insulated protecting case. The uncovered holes are exposed to the windstream alongside the head (such as during skiing); and because they are open and uncovered to the outside, each hole becomes a wind noise generator. Such heavy duty earmuffs are uncomfortable to wear in the summer.

Simpler, more traditional ear cover paraphernalia include wool caps, flat earmuffs, and headbands which pass over and press on the ear flange. By necessity, they must be somewhat snug in order to keep out the wind. The popularity of these apparel notwithstanding, many people do not like their ears pressed against their heads and prefer to go without protection.

From an aeroacoustical standpoint, depending on the surface material used, headbands and caps are fairly efficient in eliminating mid and high frequency wind noise (the blowing sound "WH") because they divert the airflow past the external ear where that specific noise is generated. But the elimination of the low frequency rumble is elusive. Heavier materials are currently being used in some common earmuffs to address this problem but the ambient high frequency sound transmission to the ear is compromised. Ironically, it is the high frequencies that allow the external ear to sense fore and aft direction of the sound source accurately, an important safety feature on the work site.

Attempts at low frequency wind noise abatement are not new. In 1954, Hayes and Cudworth* published experimental data concerning a crude windscreen design which was tested at the Acoustics Laboratory, Massachusetts Institute of Technology, under contract with the Air Force. (J. R. M. Hayes and A. L. Cudworth (1954), letters to the editor "*Windscreen for the Ear*" J. Acoust. Soc. Am. 26, 254–5.) The windscreen was made up of two cylindrical cups, each 2¾" diameter by 3½" long (20 cubic inches each). The surface, made of woven nylon cloth with negligible ambient sound attenuation, was stretched over a ¼" mesh screen matrix. Standard earphone cushions and an earphone headband provided sealed contact with the head.

Partial results of the test show that at a wind speed of 20 mph, the windscreen attenuated the wind noise of the unprotected ear canal by an average of 21 decibels (dB) at 200 cycles per second (Hz), and 13 dB at around 500 Hz. This is a significant drop in noise level, especially at the lower frequency. However, people will likely not wear such unwieldy cylinders over their ears when they can use the less effective but much simpler headband.

SUMMARY OF THE INVENTION

The present invention is directed to a wind deflector designed to offer no significant resistance to ambient sound but to facilitate an aerodynamic surface by which wind can be noiselessly bypassed along the side of the head and in particular the concha.

The wind deflector is constructed of a soundpermeable matrix covered by a generally wind impermeable, aerodynamically smooth, sound-permeable covering. The purpose of the outer surface is to allow the flow of air to slip by as noise-free as possible. The purpose of the matrix is to give a designed aerodynamic shape to the surface.

The wind deflector is placed over the entire ear and is provided with an aerodynamic leading edge which extends forward to a position at or near the cheek bone area. The center section of the ear cover, which overlaps the external ear, is sound-permeable. The leading edge section can also be sound-permeable, but it is not always necessary. The invention is especially useful for strong headwinds which can create strong turbulence behind the cheek as well as in the concha.

BRIEF DESCRIPTION OF THE DRAWINGS

FIG. 1 is an illustration of the first embodiment with a C-shaped outer section.

FIG. 2 is a cross-sectional view of FIG. 1 and is viewed along sectional line 2—2 of FIG. 1.

FIG. 3 is an illustration of the embodiment of FIG. 1 shown without the matrix material to illustrate how it surrounds the ear.

FIG. 4 is an illustration of an embodiment similar to the FIG. 1 embodiment but with alternate outer edge using an O-shaped section and shown without its matrix material.

FIG. 5 is an illustration of an example of how the embodiment of FIG. 1 might be held against the ear.

DESCRIPTION OF THE PREFERRED EMBODIMENTS

Figure 7:
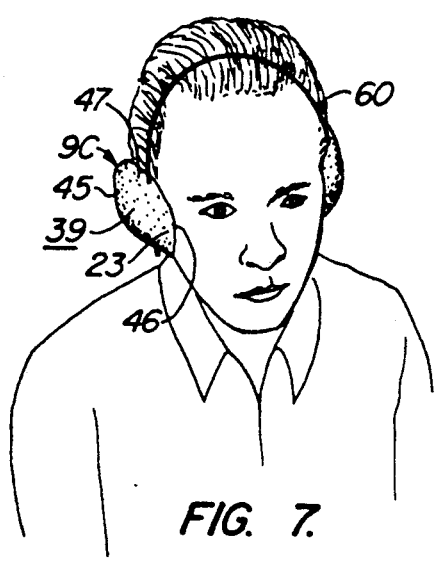
FIG. 7 illustrates the wind deflector of FIG. 6 in use.

Referring to FIGS. 1 and 3, a wind deflector 9A is shown surrounding ear 11. Deflector 9A deflects air away from ear 11 as the air passes from front to rear alongside the user's head, such as when the user is facing generally into the wind. Deflector 9A contains an outer portion 19 which partially surrounds ear 11 by passing above upper edge 13 of ear 11, under lobe 15 and in front of forward portion 17 of ear 11. This outer portion 19 contains, at the front, a leading edge 23 which initiates the deflection of wind past ear 11. FIG. 2 shows how leading edge 23 may be sloped with an appropriate aerodynamic shape to better deflect air alongside of head. The C-shaped configuration of outer portion 19 forms an open inner region 21 through which ambient sound may pass.

FIG. 2 shows the detailed cross section of the sound-permeable inner region. Outer surface 39 of deflector 9A is to generally be a smoothly curved section of an ellipsoid across which air can silently pass. Deflector 9A rests snugly against head 43 such that outer portion 19 contacts the skin or hair around ear 11. If necessary the outer portion can be constructed to contact head just behind the cheek bone area 98 in order to facilitate laminar air flow attachment along the temple area. An inner surface 41 is curved in substantially the same shape as outer surface 39. This allows inner surface 41 to fit around ear 11 without putting pressure on ear pinna 12.

Inner region 21 of deflector 9A includes a matrix 33 covered by a layer 26 of a material, such as acrylic or wool felt or a brushed cotton flannel fabric, which can provide a smooth surface over which wind will pass. Generally, even though the material 26 is fastened to the matrix, it should be low in stiffness in order to damp out drumming sound caused by residual turbulence. Matrix 33 is formed of a sound-permeable material so that ambient sound is permitted to pass therethrough to the ear. (Matrix 33 is not shown in FIGS. 3 and 4 for sake of clarity.) An example of a suitable material for matrix 33 is a polyethylene or nylon fiber mat or a shaped metal screen. Cover 26 has an outer surface 27 which continues the aerodynamic surface formed by surface 18 of outer portion 19. (Surfaces 18 and 27 constitute surface 39 of wind deflector 9A.)

Rear portion 89 of deflector 9A facilitates an open space in matrix 33 for ventilation and rear hearing purposes. Rear hearing is enhanced by reflective surface 75 (FIG. 2) which helps direct high frequency sound waves from the rear into the ear canal. Section boundaries 37 may be included to further reduce boundary layer wind noise and also to stiffen matrix 33. The stiffening members 37 can be used in combination with an ultrafine metal screen in matrix 33 to damp out the ultra low frequency pressure surges experienced in gusty winds.

FIG. 4 shows a wind deflector 9B similar to wind deflector 9A but with the outer portion 19 being O-shaped. It includes a back part 30 so as to fully encircle the ear. This is useful for deflecting gusty winds from all directions; however ventilation may be reduced.

FIGS. 1, 3, 4 show wind deflector 9A with an extension 31 which projects above the ear so that a strap 51, see FIG. 5, worn around the head, will firmly hold deflector 9A in place. Other structures for securing deflector 9A to the user's head can be used as well, such as the ear pieces of a pair of eye glasses. Also, deflector 9A could be held to the ears with a conventional ear muff band, or a helmet strap.

Figure 6:
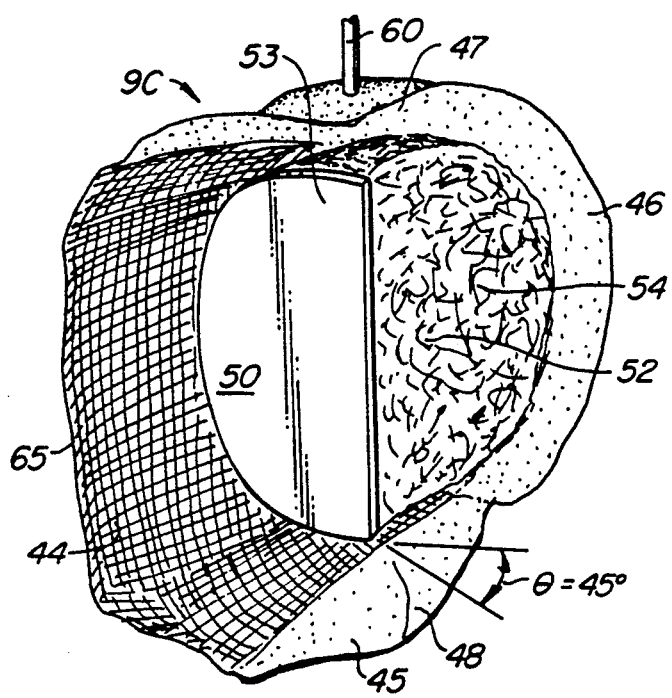
FIG. 6 is an overall perspective view of a further embodiment of the invention.
Figure 11:
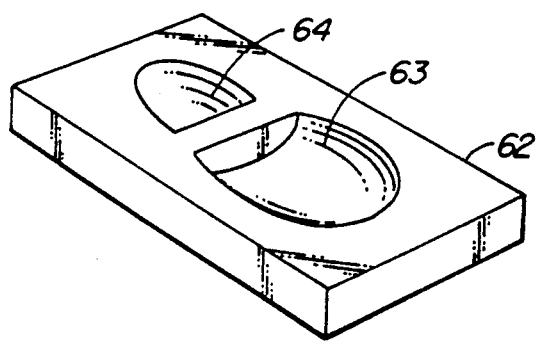
FIG. 11 shows a pattern used during the manufacture of the wind deflectors of FIGS. 6 and 8.

Turning now to FIGS. 6 and 7, a further alternative embodiment of the invention is shown. Deflector 9C is shown to include a wire mesh 44 acting as the form inducing matrix for wind defector 9C. Wire mesh 44 is covered with a felt layer 45 which defines outer surface 39. Felt layer 45 extends around the periphery of wind deflector 9C to create a forward or leading edge flap 46, an upper edge flap 47 and a lower edge flap 48. As suggested in FIG. 7, these edge flaps are flexible and somewhat resilient to snugly engage the surface of the user's head to create a reasonably tight but comfortable seal. Instead of felt layer 45, other materials which provide a sound permeable, smoothly contoured wind deflecting surface, such as fake fur, could also be used. As in 9A and 9B, a flexible low stiffness material is desirable.

The interior of wind deflector 9C includes an open rear region 50 and a filled front region 52 separated by a sound reflector 53, typically made of plastic. Sound reflector 53 is oriented at a 45° angle, as suggested in the embodiment of FIG. 9. The use of sound reflector 53 should focus into the ear canal those sounds 6000 Hz and higher which radiate from the rear. This is a safety feature which facilitates receipt of considerable sound detail of things happening behind, e.g. the tire noise of an approaching car may be heard by a bicycle rider. Region 50 houses the user's ear and is open in the rear for ventilation and ease of donning and doffing. Front region 52 could be empty as well, but, in the embodiment of FIGS. 6 and 7, is filled with a relatively stiff nylon fiber 54. Nylon fiber 54 is used, in conjunction with wire mesh 44, to provide the proper aerodynamic contour to outer surface 39. A generalized section of a paraboloid contour is preferred. Any suitably stiff, light weight material could also be used. In appropriate cases, the support provided by wire mesh 44 alone may be suitable to eliminate the need for fiber 54.

Figure 8:
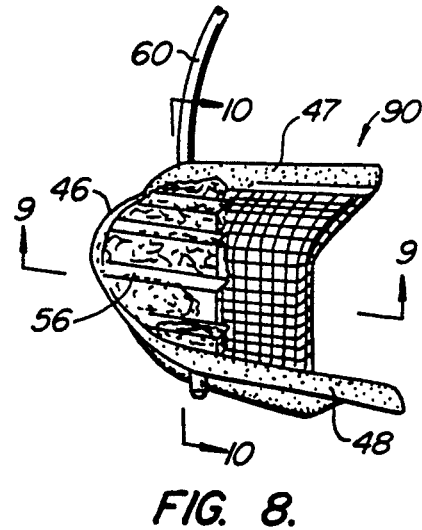
FIG. 8 is an interior perspective view of another alternative embodiment of the invention similar to the wind deflector of FIG. 6 but including risers to provide ventilation air paths through the wind deflector.
Figure 10:
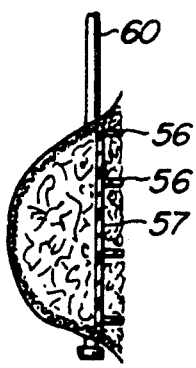
FIGS. 9 and 10 are cross-sectional views taken along lines 9—9 and 10—10 of FIG. 8.
Figure 9:
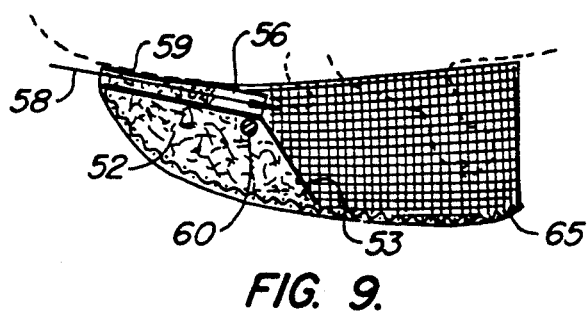

FIGS. 8-10 illustrate a further embodiment of the invention. Wind deflector 9D is similar to wind deflector 9C but with the front region 52 modified. Region 52 includes a number of plastic nylon risers 56 extending from a base 57. Sound deflector 53 is an integral extension from base 57. Risers 56 and base 57 provide shallow flow paths 58 within which a light acrylic batting 59 is placed to limit the speed of the ventilation flow. This allows flow paths 58 to provide a very low volume of noiseless air flow for cooling purposes. As suggested in FIG. 8, upper edge flap 47 and lower edge flap 48 are similar to the corresponding flaps of wind deflector 9C. However, the forward edge flap 46 of wind deflector 9D is somewhat smaller to permit a small amount of ventilating air flow along flow paths 58. FIG. 9 also shows the extension of wire headband 60, used with wind deflectors 9C and 9D, through the front region 52 of each.

In constructing wind deflectors 9C and 9D, a pattern 62 may be used. Pattern 62 includes depressions 63, 64 of different sizes for different sized wind deflectors. Wire mesh 44 is first placed into one of the depressions, such as depression 63, and formed into shape. The formed wire mesh is removed and the felt layer 45 is placed into depression 63 and formed to the contour of the depression. The preformed wire mesh 44 is then placed upon the felt layer 45 and the two bonded together, such as with an adhesive. Fiber 54 and sound deflector 53 are then positioned within the wire mesh 44 at front region 52 and are secured in place, typically with an adhesive.

As shown in FIGS. 7, 8 and 9, pivotable headband 60 is positioned forward of the center of wind deflectors 9C, 9D. This is important to ensure a good tight seal between forward edge flap 46 and the user's head to keep turbulence away from the ear canal. FIG. 9 also illustrates how the trailing edge 65 at the rear portion 89 is preferably tapered inwardly. This allows one to turn his or her head without creating excessive shedding or whistling noise, which could be created if the trailing edge 65 extended straight back.

Experiments were conducted using a wind deflector 9C modified only by using an acrylic pile layer instead of felt layer 45. The acrylic pile layer was made of a synthetic fur material with surface fibers about two inches long and combed in the direction of the airflow. Ambient sound transmission through pile 45 was unattenuated up to the highest frequency tested, 8000 Hz.

The wind deflector was tested in a head-on windstream. The wind deflector was compared to a wool knit headband in a 12 mph wind, which was created by bicycling in still air at 12 mph. Only two ounces of force was required to hold the wind deflector against the head. The acoustic test equipment consisted of a loudspeaker mounted behind the shoulder-neck area which was driven by an audio sine wave oscillator. Following the method of Hayes, et al., single audio tones were serially intensified until the selected tone was just barely audible through the wind noise in the ear canal. The tone intensities were compared with the background used as threshold noise in the relation $db = 20 \log (I_t/I_b)$, where $I_t$ is tone intensity and $I_b$ is background intensity. The experiment was repeated with the wind deflector or wool headband in place. The chart below shows the wind noise above threshold at two frequencies. Threshold sound was freeway noise one mile away. Noise levels are in dB.

| Wind noise level in decibels above remote freeway noise as a function of 12 mph wind velocity, stimulus frequency and ear covering. | | |
| --- | --- | --- |
| frequency (Hz) | 103 | 215 |
| bare head | 29.95 | 37.3 |
| headband | 18.66 | 14.8 |
| wind deflector | 6.6 | 7.35 |

The field test shows that the wind deflector is significantly quieter than the wool headband, especially at the lower frequency. Not only was the wind noise dramatically reduced with the deflector, but the variability or infrasonic variation was also diminished proportionately, which for many people is more important from the irritation and fatigue standpoint. This is especially true in atmospheric wind. Although at 12 mph this noise is not loud by modern industrial standards, Table I of Hayes, et al. shows that ear canal noise can double and triple at 20 mph and 40 mph respectively.

Modification and variation can be made to the disclosed embodiments without departing from the subject of the invention as defined by the following claims.

What is claimed is:

1. An apparatus for reducing wind noise with respect to a user's ear, the ear having an upper edge, an ear lobe, and a front part, the apparatus comprising:
    a wind deflector including,
        an outer portion configured to at least partially surround at least the upper edge of the ear, the ear lobe and the front part of the ear, said outer portion having a smooth outer surface shaped such that wind flows smoothly over said outer surface;
        a sound-permeable inner portion attached to the outer portion and located alongside the user's ear, said inner portion having a smooth outer surface flush with the smooth outer surface of the outer portion; and
        means for creating an air flow ventilation path between the user's head and the inner portion; and
    securing means, located on the outer portion, for securing said wind deflector to the user's head.

2. The apparatus of claim 1, wherein said securing means further comprises a head band which fits over the top of the head, said band having a first end and a second end, one of said ends terminating on either side of the head adjacent the ear.

3. The apparatus of claim 1 wherein said outer portion is formed from a substantially rigid material allowing said outer portion to retain its shape.

4. The apparatus of claim 1, wherein said outer portion is generally C-shaped.

5. The apparatus of claim 1, wherein said wind deflector includes a rearwardly facing sound reflecting surface positioned and shaped to help sound coming in from the rear of the user's head to be reflected into the user's ear.

6. The apparatus of claim 1, wherein said outer portion fully encircles the outside of the ear and is generally O-shaped.

7. The apparatus of claim 1, wherein said inner portion includes a mesh material.

8. The apparatus of claim 1, wherein said outer portion has a substantially flat generally annular inner surface which contacts the head about the ear of the user.

9. The apparatus of claim 1 wherein the combined outer surfaces of the outer and inner portions are generally a section of an ellipsoid in shape.

10. The apparatus of claim 1, further comprising means for creating an air flow ventilation path between the user's head and the wind deflector.

11. An apparatus worn on a user's head for reducing noise caused by wind flowing past the user's ear, the ear having an upper edge, an ear lobe, a front part, and a rear part, the apparatus comprising:
a wind deflector including:
a sound-permeable shell overlying the ear,
said shell having a peripheral edge contacting the user's head from a first point above the upper edge of the ear to a second point in front of the front part of the ear to a third point below the ear lobe,
said shell having an outer surface rising smoothly from the second point to a fourth point overlying the rear part of the ear to facilitate wind flow over the ear,
said shell having an interior sized to house the ear,
means for creating an air flow ventilation path between the user's head and the inner portion; and
said shell providing a smooth, substantially protuberance free, wind deflecting, substantially acoustically transparent surface for deflecting wind past the user's ear to minimize wind noise while not substantially hindering sound travel to the ear; and
securing means, attached to the peripheral edge of the shell, for securing said wind deflector to the user's head.

12. The apparatus of claim 11, wherein the entire shell comprises said acoustically transparent surface.

13. The apparatus of claim 11, wherein the shell has a rear portion at or near the rear part of the user's ear, said rear portion being substantially open to facilitate the user's hearing of sounds from the rear, ventilation, and ease of donning and doffing.

14. The apparatus of claim 11, wherein the shell includes a stiff yet resilient mesh material.

15. The apparatus of claim 14, wherein the shell includes a fabric covering the stiff resilient mesh material, the fabric extending beyond the peripheral edge to form a wind seal flap flush with the user's head.

16. The apparatus of claim 11, further including a flexible edge seal at the peripheral edge to help seal the peripheral edge against the user's head.

17. The apparatus of claim 16, wherein the edge seal includes a flap of fabric.

18. The apparatus of claim 11 further comprising a curve at the rear edge of the shell to minimize turbulence when the user's head is turned.

19. The apparatus of claim 11 wherein the outer surface of the shell is generally a section of a paraboloid in shape.

20. The apparatus of claim 11, wherein the securing means further comprises a head band which fits over the user's head.

21. The apparatus of claim 11, wherein the securing means is a headband which is pivotable about the vertical axis with respect to the ear cover.

22. The apparatus of claim 11, wherein the securing means further comprises holes through which a strap may pass n a substantially vertical direction.

23. An apparatus worn on a user's head for reducing noise caused by wind flowing past the user's ear, the ear having an upper edge, an ear lobe, a front part, and a rear part, the apparatus comprising:
a wind deflector including:
a sound-permeable shell overlying the ear,
said shell having a peripheral edge contacting the user's head from a first point above the upper edge of the ear to a second point in front of the front part of the ear to a third point below the ear lobe,
said shell having an outer surface rising smoothly from the second point to a fourth point overlying the rear part of the ear to facilitate wind flow over the ear,
said shell having an interior sized to house the ear,
said shell providing a smooth, substantially protuberance free, wind deflecting, substantially acoustically transparent surface for deflecting wind past the user's ear to minimize wind noise while not substantially hindering sound travel to the ear, and
said shell having a rear portion at or near the rear part of the user's ear, said rear portion being substantially open to facilitate the user's hearing of sounds from the rear, ventilation, and ease of donning and doffing;
securing means, attached to the peripheral edge of the shell, for securing said wind deflector to the user's head; and
a sound reflecting surface defining a forward portion of said interior configured to reflect sounds towards the user's ear.

24. An apparatus worn on a user's head for reducing noise caused by wind flowing past the user's ear, the ear having an upper edge, an ear lobe, a front part, and a rear part, the apparatus comprising:
a wind deflector including:
a sound-permeable shell overlying the ear,
said shell having an outer surface rising smoothly from a first point to a second point overlying the rear part of the ear to facilitate wind flow over the ear,
said shell having an interior sized to house the ear, and
at least a portion of said outer surface being acoustically transparent;
securing means, attached to said shell for securing said wind deflector to the user's head; and
a sound reflecting surface defining a portion of said interior configured to reflect sounds towards the user's ear.

25. Apparatus for reducing wind noise caused by wind flowing past a user's ear when the user is facing into the wind, the ear having an upper edge, an ear lobe, a front part and a rear part, the apparatus comprising:
a shell sized to cover the ear, said shell being open at the rear part of the user's ear, said shell including:

a peripheral edge which contacts the user's head from a first point in the region of the upper edge of the ear, to a second point forward of the forward portion of the ear, and to a third point in the region of the ear lobe; and a smoothly curving, generally a section of a paraboloid in shape, substantially acoustically transparent surface means for smoothly deflecting the wind past the ear to minimize wind noise while not substantially attenuating ambient sounds; and means connected to the shell adjacent the peripheral edge for securing the shell to the user's head, said securing means including:

means for sealing said peripheral edge of said shell against the user's head, and a means for reflecting sound back towards the user's ear.

26. Apparatus for reducing wind noise caused by wind flowing past a user's ear when the user is facing into the wind, the ear having an upper edge, an ear lobe, a front part and a rear part, the apparatus comprising:

a shell sized to cover the ear, wherein said shell is open at the rear part of the user's ear and said shell has a smoothly curving, generally a section of a paraboloid in shape, substantially acoustically transparent surface means for smoothly deflecting the wind past the ear to minimize wind noise while not substantially attenuating ambient sounds; and means connected to the shell adjacent the peripheral edge for securing the shell to the user's head, said securing means including:

means for sealing said peripheral edge of said shell against the user's head, and a means for reflecting sound back towards the user's ear.

* * * * *